United States Patent
Bae et al.

(10) Patent No.: US 9,943,260 B2
(45) Date of Patent: *Apr. 17, 2018

(54) METHOD FOR JUDGMENT OF DRINKING USING DIFFERENTIAL ENERGY IN TIME DOMAIN, RECORDING MEDIUM AND DEVICE FOR PERFORMING THE METHOD

(71) Applicant: Foundation of Soongsil University-Industry Cooperation, Seoul (KR)

(72) Inventors: Myung Jin Bae, Seoul (KR); Sang Gil Lee, Busan (KR); Seong Geon Bae, Seoul (KR)

(73) Assignee: FOUNDATION OF SOONGSIL UNIVERSITY—INDUSTRY COOPERATION, Seoul (KR)

( * ) Notice: Subject to any disclaimer, the term of this patent is extended or adjusted under 35 U.S.C. 154(b) by 0 days.

This patent is subject to a terminal disclaimer.

(21) Appl. No.: 15/300,217

(22) PCT Filed: Apr. 2, 2014

(86) PCT No.: PCT/KR2014/002851
§ 371 (c)(1),
(2) Date: Sep. 28, 2016

(87) PCT Pub. No.: WO2015/147364
PCT Pub. Date: Oct. 1, 2015

(65) Prior Publication Data
US 2017/0135620 A1    May 18, 2017

(30) Foreign Application Priority Data

Mar. 28, 2014  (KR) .................. 10-2014-0036631

(51) Int. Cl.
*A61B 5/18* (2006.01)
*A61B 5/00* (2006.01)
(Continued)

(52) U.S. Cl.
CPC .............. *A61B 5/18* (2013.01); *A61B 5/4803* (2013.01); *A61B 5/4845* (2013.01);
(Continued)

(58) Field of Classification Search
CPC ....................................................... G10L 17/26
See application file for complete search history.

(56) References Cited

U.S. PATENT DOCUMENTS 5,776,055 A   7/1998  Hayre
5,913,188 A   6/1999  Tzirkel-Hancock
(Continued)

FOREIGN PATENT DOCUMENTS

EP   1850328 A1   10/2007
JP   2003-36087 A   2/2003
(Continued)

OTHER PUBLICATIONS

Baumeister, Barbara, Christian Heinrich, and Florian Schiel. "The influence of alcoholic intoxication on the fundamental frequency of female and male speakers." The Journal of the Acoustical Society of America 132.1 (2012): 442-451.*
(Continued)

*Primary Examiner* — Matthew Baker
(74) *Attorney, Agent, or Firm* — Novick, Kim & Lee, PLLC; Sang Ho Lee

(57) ABSTRACT

An alcohol consumption determination method includes detecting a plurality of effective frames of an input voice signal; detecting a difference in signal of within the original signal of each of the effective frames; detecting average energy of the original signal and average energy of the
(Continued)

difference signal for each of the effective frames; and determining whether alcohol has been consumed based on a difference between the average energy of the original signal and the average energy of the difference between the signals for each effective frame. Accordingly, it is also possible to determine, from a remote location, whether a driver or an operator remote has consumed alcohol and the degree of inebriation by using a difference signal energy method using a voice signal, thus preventing an accident caused by a operation vehicles and machines under the influence of alcohol.

18 Claims, 4 Drawing Sheets

(51) Int. Cl.
G10L 25/21 (2013.01)
G10L 25/66 (2013.01)
B60K 28/06 (2006.01)
G10L 25/30 (2013.01)

(52) U.S. Cl.
CPC ............ *A61B 5/7264* (2013.01); *G10L 25/21* (2013.01); *G10L 25/30* (2013.01); *G10L 25/66* (2013.01); *B60K 28/06* (2013.01)

(56) References Cited

U.S. PATENT DOCUMENTS

| | | | | |
|---|---|---|---|---|
| 5,983,189 | A * | 11/1999 | Lee | G08B 21/06 704/273 |
| 6,006,188 | A | 12/1999 | Bogdashevsky | |
| 6,205,420 | B1 | 3/2001 | Takagi | |
| 6,275,806 | B1 | 8/2001 | Pertrushin | |
| 6,446,038 | B1 | 9/2002 | Bayya | |
| 6,748,301 | B1 | 6/2004 | Ryu | |
| 7,925,508 | B1 * | 4/2011 | Michaelis | G10L 17/26 600/300 |
| 7,962,342 | B1 * | 6/2011 | Coughlan | G10L 15/22 379/201.01 |
| 8,478,596 | B2 | 7/2013 | Schultz | |
| 8,938,390 | B2 | 1/2015 | Xu | |
| 9,058,816 | B2 | 6/2015 | Lech | |
| 9,659,571 | B2 | 5/2017 | Van Der Schaar | |
| 9,672,809 | B2 | 6/2017 | Togawa et al. | |
| 2002/0010587 | A1 | 1/2002 | Pertrushin | |
| 2002/0194002 | A1 | 12/2002 | Petrushin | |
| 2003/0069728 | A1 | 4/2003 | Tato | |
| 2004/0167774 | A1 | 8/2004 | Shrivastav | |
| 2005/0075864 | A1 | 4/2005 | Kim | |
| 2005/0102135 | A1 | 5/2005 | Goronzy | |
| 2007/0071206 | A1 | 3/2007 | Gainsboro | |
| 2007/0124135 | A1 | 5/2007 | Schultz | |
| 2007/0192088 | A1 | 8/2007 | Oh | |
| 2007/0213981 | A1 | 9/2007 | Meyerhoff | |
| 2007/0288236 | A1 | 12/2007 | Kim | |
| 2009/0265170 | A1 | 10/2009 | Irie | |
| 2010/0010689 | A1 * | 1/2010 | Yasushi | B60K 28/063 701/1 |
| 2011/0035213 | A1 | 2/2011 | Malenovsky | |
| 2011/0282666 | A1 | 11/2011 | Washio | |
| 2012/0089396 | A1 | 4/2012 | Patel | |
| 2012/0116186 | A1 | 5/2012 | Shrivastav | |
| 2012/0262296 | A1 | 10/2012 | Bezar | |
| 2013/0006630 | A1 | 1/2013 | Hayakawa | |
| 2013/0253933 | A1 | 9/2013 | Maruta | |
| 2014/0122063 | A1 | 5/2014 | Gomez Vilda | |
| 2014/0188006 | A1 | 7/2014 | Alshaer | |
| 2014/0379348 | A1 | 12/2014 | Sung | |
| 2015/0127343 | A1 * | 5/2015 | Mullor | G10L 17/26 704/244 |
| 2015/0257681 | A1 * | 9/2015 | Shuster | A61B 5/1123 600/301 |
| 2015/0310878 | A1 | 10/2015 | Bronakowski | |
| 2015/0351663 | A1 | 12/2015 | Zigel | |
| 2016/0155456 | A1 | 6/2016 | Wang | |
| 2016/0379669 | A1 * | 12/2016 | Bae | G10L 17/26 704/232 |
| 2017/0004848 | A1 * | 1/2017 | Bae | G10L 25/48 |

FOREIGN PATENT DOCUMENTS

| | | |
|---|---|---|
| JP | 2010-015027 A | 1/2010 |
| JP | 5017534 B2 | 9/2012 |
| KR | 10-1997-0038004 A | 7/1997 |
| KR | 10-0201256 B1 | 6/1999 |
| KR | 10-1999-0058415 A | 7/1999 |
| KR | 10-0206205 B1 | 7/1999 |
| KR | 2004-0033783 A | 4/2004 |
| KR | 10-0497837 B1 | 6/2005 |
| KR | 10-0664271 B1 | 1/2007 |
| KR | 10-2009-0083070 A | 8/2009 |
| KR | 10-2012-0074314 A | 7/2012 |
| WO | 2012/014301 A1 | 2/2012 |

OTHER PUBLICATIONS

Schuller, Björn W., et al. "The INTERSPEECH 2011 Speaker State Challenge." INTERSPEECH. 2011.*
Hollien, Harry, et al. "Effects of ethanol intoxication on speech suprasegmentals." The Journal of the Acoustical Society of America 110.6 (2001): 3198-3206.*
Seong Geon Bae, Dissertation for Ph.D, "A study on Improving Voice Surveillance System Against Drunk Sailing". Information and Communication Engineering Dept., Soongsil University, Republic of Korea. Dec. 2013. (English Abstract at pp. x-xii).
Lee, Won Hui et al. "Valid-frame Distance Deviation of Drunk and non-Drunk Speech" The Journal of Korea Information and Communications Society (winter) 2014, pp. 876-877, Jan. 2014.
Geumran Baek et al. "A Study on Judgment of Intoxication State Using Speech," Information and Telecommunication Department, Soongsil University, pp. 277-282.
Seong-Geon Bae et al. "A Study on Personalized Frequency Bandwidth of Speech Signal using Formant to LPC," The Journal of Korean Institute of Communications and Information Sciences (winter), 2013, pp. 669-670.
Seong-Geon Bae et al. "A Study on Drinking Judgement Method of Speech Signal Using the Fomant Deviation in the Linear Prediction Coefficient," he Journal of Korean Institute of Communications and Information Sciences (winter), 2013, pp. 667-668.
Jung, Chan Joong et al. "A Study on Detecting Decision Parameter about Drinking in Time Domain," The Journal of Korea Information and Communications Society (winter) 2014, pp. 784-785, Jan. 2013.
Bocklet, Tobias, Korbinian Riedhammer, and Elmar Noth. "Drink and Speak: On the automatic classification of alcohol intoxication by acoustic, prosodic and text-based features." Twelfth Annual Conference of the International Speech Communication Association. 2011.
Geumran Baek et al. "A Study on Voice Sobriety Test Algorithm in a Time-Frequency Domain" International Journal of Multimedia and Ubiquitous Engineering vol. 8 No. 5 (2013), pp. 395-402.
Tae-Hun Kim et al. "Drinking Speech System", Department of Information Communication, Sang Myung University, pp. 257-262.
Chan Joong Jung et al. "Speech Sobriety Test Based on Formant Energy Distribution" International Journal of Multimedia and Ubiquitous Engineering vol. 8 No. 6 (2013), pp. 209-216.
Kim (Kim, Jonathan, Hrishikesh Rao, and Mark Clements. "Investigating the use of formant based features for detection of affective dimensions in speech." Affective computing and intelligent interaction (2011): 369-377.).
Broad (Broad, David J., and Frantz Clermont. "Formant estimation by linear transformation of the LPC cepstrum." The Journal of the Acoustical Society of America 86.5 (1989)).

(56) References Cited

OTHER PUBLICATIONS

Sato (Sato, Nobuo, and Yasunari Obuchi. "Emotion recognition using mel-frequency cepstral coefficients." Information and Media Technologies 2.3 (2007): 835-848.).

Lee, Won-Hee et al.."A Study on Drinking Judgement using Differential Signal in Speech Signal", The Journal of Korea Information and Communications Society (winter) 2014, pp. 878-879, Jan. 2014.

Chan Joong Jung et al. "A Study on Drunken Decision using Spectral Envelope Changes" Korea Institute of Communications and Information Sciences, Winter Conference, vol. 2013 No. 1 (2013), pp. 674-675.

See-Woo Lee, "A Study on Formant Variation with Drinking and Nondrinking Condition," Department of Information & Telecommunication Engineering, Sangmyung University, vol. 10, No. 4, pp. 805-810, 2009.

\* cited by examiner

METHOD FOR JUDGMENT OF DRINKING USING DIFFERENTIAL ENERGY IN TIME DOMAIN, RECORDING MEDIUM AND DEVICE FOR PERFORMING THE METHOD

TECHNICAL FIELD

The present invention relates to a method of determining whether alcohol has been consumed and a recording medium and device for performing the same, and more particularly, to a method of determining whether alcohol has been consumed by using a difference signal energy method using a voice and a recording medium and device for performing the same.

BACKGROUND ART

Although consuming a moderate amount of alcohol offers various benefits to people, excessive consumption is harmful to one's health. In addition, drunk driving causes fatal accidents and, in some cases, even death.

As for methods of measuring drunkenness, there is a method of measuring the concentration of alcohol in exhaled air during respiration using a breathalyzer equipped with an alcohol sensor and there is a method of measuring the concentration of alcohol in the blood flow using a laser.

Generally, the former method is usually used for cracking down on drunk driving. In this case, when any driver refuses a sobriety test, the Widmark Equation may be used to estimate a blood alcohol concentration by collecting the blood of the driver with his or her consent.

Accidents caused by operating a vehicle under the influence of alcohol at sea or in the air, in addition to vehicular accidents, are also problematic. However, an existing alcohol consumption measurement method requires testing the operator in person and thus, is not suitable for determining whether an operator at a remote location is drunk.

Accordingly, the government is exerting various efforts to prevent operating a vehicle under the influence of alcohol at sea or in the air. As one of the efforts, for a vessel, cracking down on a operating a vehicle under the influence of alcohol is performed by measuring alcohol consumption before and after operation. However, the measurement is difficult during the time the individual is actively operating the vehicle.

In some cases, the Coast Guard may perform random sobriety checks through direct contact at sea. However, this method is very dangerous due to the difficulty of making vessel-to-vessel contact and a flight risk from the vessel. Accordingly, determining whether alcohol has been consumed is indirectly ascertained via communication with an operator at sea. However, it is difficult to determine whether alcohol has been consumed when the operator denies drinking alcohol. Thus, there is a need for a method of indirectly and objectively determining whether an operator, even from a long distance, has consumed alcohol.

DISCLOSURE

Technical Problem

The present invention is directed to providing an alcohol consumption determination method for determining whether alcohol has been consumed and the degree of the consumption by analyzing an operator's voice taken over communication.

The present invention is also directed to providing a recording medium having a computer program recorded thereon for performing the alcohol consumption determination method.

The present invention is also directed to providing a device for performing the alcohol consumption determination method.

Technical Solution

According to an embodiment for achieving the above-described objective of the present invention, an alcohol consumption determination method includes detecting a plurality of effective frames of an input voice signal; detecting a difference signal of an original signal of each of the effective frames; detecting average energy of the original signal and average energy of the difference signal for each of the effective frames; and determining whether alcohol has been consumed based on a difference between the average energy of the original signal and the average energy of the difference signal for each of the effective frames.

The determining of whether alcohol has been consumed may include comparing the average energy of the original signal and the average energy of the difference signal for each effective frame and outputting a difference in the average energy; counting the number of effective frames each having the difference between the average energy of the original signal and the average energy of the difference signal greater than a predetermined first threshold; and determining that alcohol has been consumed when the counted number of effective frames is greater than a predetermined second threshold and outputting a result of the determination.

The determining of whether alcohol has been consumed may include comparing the average energy of the original signal and the average energy of the difference signal for each effective frame and outputting a difference in the average energy; counting the number of effective frames each having the difference between the average energy of the original signal and the average energy of the difference signal greater than a predetermined first threshold; comparing the counted number of effective frames with the total number of effective frames to calculate a ratio therebetween; and determining that alcohol has been consumed when the ratio is greater than a predetermined third threshold and outputting a result of the determination.

The detecting of an effective frame may include forming a voice frame of the input voice signal; and determining whether the voice frame corresponds to a voiced sound.

The detecting of a difference signal may include generating a shift signal S(n−1) by shifting the original signal S(n) of the effective frame; and outputting a difference signal S(n)−S(n−1) between the original signal and the shift signal.

The detecting of average energy of the original signal and average energy of the difference signal for each of the effective frames may include detecting the average energy of the original signal for each effective frame; and detecting the average energy of the difference signal for each effective frame.

According to an embodiment for achieving the above-described other objective of the present invention, there is a computer-readable recording medium having a computer program recorded thereon for performing the above-described alcohol consumption determination method.

According to an embodiment for achieving the above-described still other objective of the present invention, an alcohol consumption determination device includes an effective frame detection unit configured to detect a plurality of effective frames of an input voice signal; a difference signal detection unit configured to detect a difference signal of an original signal of each of the effective frames; an energy detection unit configured to detect average energy of the original signal and average energy of the difference signal for each of the effective frames; and an alcohol consumption determination unit configured to determine whether alcohol has been consumed based on a difference between the average energy of the original signal and the average energy of the difference signal for each of the effective frames.

The alcohol consumption determination unit may include an energy comparison unit configured to compare the average energy of the original signal and the average energy of the difference signal for each effective frame and outputting a difference in the average energy; a counting unit configured to count the number of effective frames each having the difference between the average energy of the original signal and the average energy of the difference signal greater than a predetermined first threshold; and a result output unit configured to determine that alcohol has been consumed when the counted number of effective frames is greater than a predetermined second threshold and outputting a result of the determination.

The alcohol consumption determination unit may include an energy comparison unit configured to compare the average energy of the original signal and the average energy of the difference signal for each effective frame and outputting a difference in the average energy; a counting unit configured to count the number of effective frames each having the difference between the average energy of the original signal and the average energy of the difference signal greater than a predetermined first threshold; a ratio calculation unit configured to compare the counted number of effective frames with the total number of effective frames to calculate a ratio therebetween; and a result output unit configured to determine that alcohol has been consumed when the ratio is greater than a predetermined third threshold and outputting a result of the determination.

The alcohol consumption determination unit may further include a storage unit configured to prestore at least one of the first threshold, the second threshold, and the third threshold.

The effective frame detection unit may include a frame forming unit configured to form a voice frame of the input voice signal; and a voiced sound determination unit configured to determine whether the voice frame corresponds to a voiced sound.

The difference signal detection unit may include a shift signal unit configured to generate a shift signal $S(n-1)$ by shifting the original signal $S(n)$ of the effective frame; and a difference signal output unit configured to output a difference signal $S(n)-S(n-1)$ between the original signal and the shift signal.

The energy detection unit may include a first energy detection unit configured to detect the average energy of the original signal for each effective frame; and a second energy detection unit configured to detect the average energy of the difference signal for each effective frame.

Advantageous Effects

According to the present invention, it is possible to determine whether a driver or operator at a remote location has consumed alcohol and the degree of the consumption, and apply voices before and after drinking to those that are speaker independent and speaker dependent by using a difference signal energy comparison method in order to highlight high frequencies of the voice signal and also increase analysis accuracy for the signal when whether alcohol has been consumed is determined in the time domain.

Accordingly, it is also possible to extract a voice of a driver or an operator at a remote location over communication to indirectly and objectively determine whether alcohol has been consumed, thus preventing an accident caused by a drunk operation.

MODES FOR CARRYING OUT THE INVENTION

Figure 1:
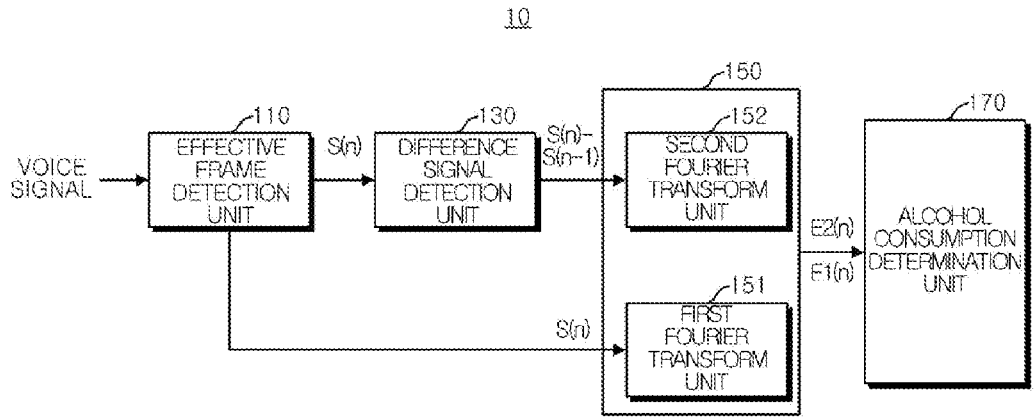
FIG. 1 is a block diagram showing a device for determining alcohol consumption according to an embodiment of the present invention.

The following detailed description refers to the accompanying drawings that illustrate exemplary embodiments consistent with the present invention. These embodiments will be described in sufficient detail to enable those skilled in the art to practice the present invention. It is to be understood that the various embodiments of the present invention, although different, are not necessarily mutually exclusive. For example, a particular feature, structure or characteristic described herein in connection with one embodiment may be implemented within other embodiments without departing from the spirit and scope of the present invention. In addition, it is to be understood that the location or arrangement of individual elements within each disclosed embodiment may be modified without departing from the spirit and scope of the present invention. The following detailed description is, therefore, not to be taken in a limiting sense, and the scope of the present invention is defined only by the appended claims, appropriately interpreted, along with the full range of equivalents to which the claims are entitled. In the drawings, like numerals refer to the same or similar elements throughout the several views.

Hereinafter, preferred embodiments of the present invention will be described in more detail with reference to the accompanying drawings.

FIG. 1 is a block diagram showing a device for determining alcohol consumption according to an embodiment of the present invention.

Referring to FIG. 1, a device 10 for determining alcohol consumption according to this embodiment includes an effective frame detection unit 110 configured to detect a plurality of effective frames of an input voice signal, a difference signal detection unit 130 configured to detect a difference signal of an original signal of each of the effective frames, an energy detection unit 150 configured to detect average energy of the original signal and average energy of the difference signal for each effective frame, and an alcohol consumption determination unit 170 configured to determine whether alcohol has been consumed on the basis of a difference between the average energy of the original signal and the average energy of the difference signal for each effective frame.

Alcohol consumption determination software (application) may be installed and executed in the device 10 according to the present invention. Elements such as the effective frame detection unit 110 may be controlled by the alcohol consumption determination software executed in the device 10.

The device 10 may be a separate terminal or a module of a terminal. The device 10 may be fixed or may have mobility. The device 10 may be referred to by other terms such as a terminal, a user equipment (UE), a mobile station (MS), a mobile terminal (MT), a user terminal (UT), a subscriber station (SS), a wireless device, a personal digital assistant (PDA), a wireless modem, a handheld device, or the like.

The device 10 may support wired or wireless communication and may include an electronic device such as a desktop computer and a smart TV in addition to various mobile devices such as a smartphone, a cellular phone, a tablet PC, a notebook, a netbook, a personal digital assistant (PDA), a portable multimedia player (PMP), a Play Station Portable (PSP), an MP3 player, an e-book reader, a navigation device, a smart camera, an electronic dictionary, an electronic watch, and a game console.

The device 10 may execute various applications on the basis of an operating system (OS). The OS is a system program for allowing an application to use a device's hardware and may include mobile computer operating systems such as iOS, Android OS, Window Mobile OS, Bada OS, Symbian OS, and Blackberry OS and computer operating systems such as Windows series, Linux series, Unix series, MAC, AIX, and HP-UX.

The application is a program that is developed to perform a specific task using a terminal, and may include various kinds of multimedia content such as games, videos, and photographs or execution programs such as an image viewer and a video player for executing the multimedia content, in addition to various kinds of application programs and service objects. It will be appreciated that the application may include all application programs and execution programs.

The effective frame detection unit 110 detects and outputs a plurality of effective frames of a user's input voice signal. The voice signal may be input to the device 10 either directly or through communication. That is, the voice signal may be input through a microphone included in the device 10 or may be transmitted from a remote location.

Figure 2:
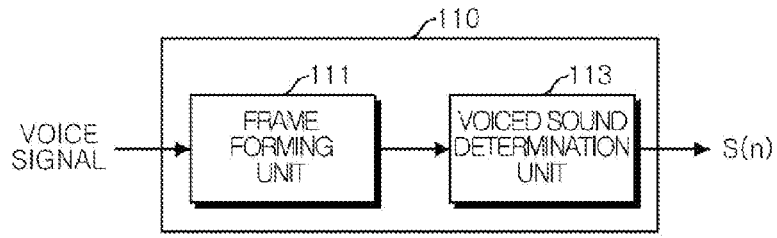
FIG. 2 is a detailed block diagram of an effective frame detection unit of FIG. 1.

Referring to FIG. 2, the effective frame detection unit 110 includes a frame forming unit 111 configured to form a voice frame of the input voice signal and a voiced sound determination unit 113 configured to determine whether the voice frame corresponds to a voiced sound.

The frame forming unit 111 receives a person's voice, converts the received voice into voice data, converts the voice data into voice frame data in units of frames, and outputs the voice frame data. Typically, analog voice signals are sampled at a rate of 8000 per second and in the size of 16 bits (65535 steps) and converted into voice data.

The frame forming unit 111 may convert a received voice signal into voice data and convert the voice data into voice frame data in units of frames. Here, one piece of the voice frame data has 256 energy values.

Figure 3:
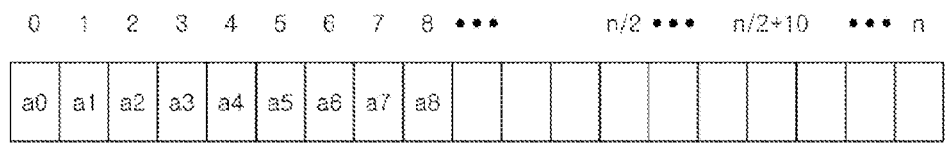
FIG. 3 is a view for describing a concept in which a frame forming unit of an effective frame detection unit of FIG. 2 converts a voice signal into a voice frame.

As shown in FIG. 3, the voice data is composed of a plurality of voice frames (n=the number of frames, n=1, 2, 3, ... ) according to the received voice. The frame forming unit 111 generates a voice frame and then outputs information regarding the voice frame to the voiced sound determination unit 113.

The voiced sound determination unit 113 receives a voice frame, extracts predetermined features from the voice frame, and analyzes whether the received voice frame is associated with a voiced sound, an unvoiced sound, or noise according to the extracted features. According to a result of the analysis, the voiced sound determination unit 113 may separate only a frame corresponding to a voiced sound from the voice frames and output the separated frame.

Figure 4:
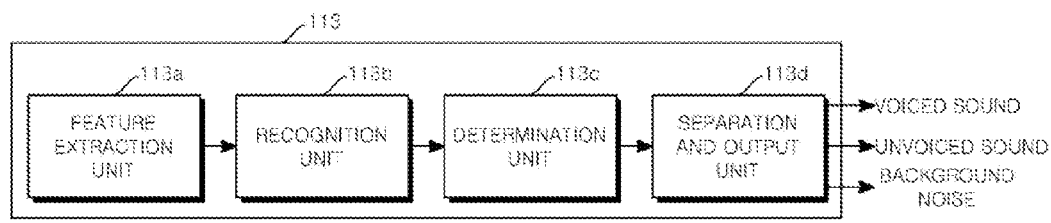
FIG. 4 is a detailed block diagram of a voiced sound determination unit of the effective frame detection unit of FIG. 2.

Referring to FIG. 4, the voiced sound determination unit 113 may include a feature extraction unit 113a configured to receive a voice frame and extract predetermined features from the voice frame, a recognition unit 113b configured to yield a recognition result for the voice frame, a determination unit 113c configured to determine whether the received voice frame is associated with a voiced sound or an unvoiced sound or whether the received voice frame is caused by background noise, and a separation and output unit 113d configured to separate and output an effective frame according to a result of the determination.

When the voice frame is received through the frame forming unit 111, the feature extraction unit 113a may extract, from the received voice frame, periodic characteristics of harmonics or features such as root mean square energy (RMSE) or zero-crossing count (ZC) of a low-band voice signal energy area.

Generally, the recognition unit 113b may be composed of a neural network. This is because the neural network is useful in analyzing non-linear problems (i.e., complicated problems that cannot be solved mathematically) and thus is suitable for analyzing voice signals and determining whether a corresponding voice signal is determined as a voiced signal, an unvoiced signal, or background noise according to a result of the analysis. The recognition unit 113b, which is composed of such a neural network, may assign predetermined weights to the features extracted from the feature extraction unit 113a and may yield a recognition result for the voice frame through a calculation process of the neural network. Here, the recognition result refers to a value that is obtained by calculating calculation elements according to the weights assigned to the features of each voice frame.

The determination unit 113c determines whether the received voice signal corresponds to a voiced sound or an unvoiced sound according to the above-described recognition result, that is, the value calculated by the recognition unit 113b. The separation and output unit 113d separates the voice frame as a voiced sound, an unvoiced sound, or background noise according to a result of the determination of the determination unit 113c.

Meanwhile, since the voiced sound is distinctly different from the voiced sound and the background noise in terms of various features, it is relatively easy to identify the voiced sound, and there are several well-known techniques for this. For example, the voiced sound has periodic characteristics in which harmonics are repeated at every certain frequency interval while the background noise does not have the harmonics.

On the other hand, the unvoiced sound has harmonics with weak periodicity. In other words, the voiced sound is characterized in that the harmonics are repeated within one frame while the unvoiced sound is characterized in that the characteristics of the voiced sound such as the harmonics are repeated every certain number of frames, that is, is shown to be weak.

When the voiced sound determination unit 113 separates a voiced sound, an unvoiced sound, or background noise, the effective frame detection unit 110 outputs only a frame for a voiced sound. The output frame for the voiced sound is referred to as an original signal S(n) of the effective frame, and the original signal S(n) of the effective frame is transferred to the difference signal detection unit 130.

Figure 5:
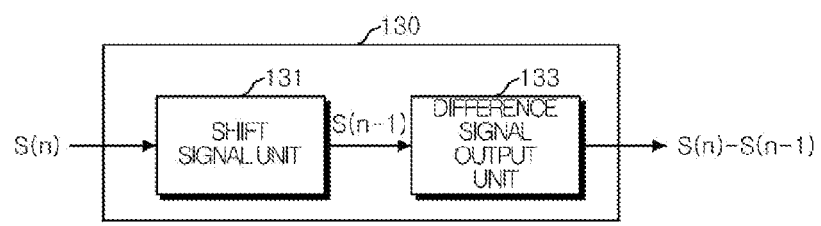
FIG. 5 is a detailed block diagram of a difference signal detection unit of FIG. 1.

Referring to FIG. 5, the difference signal detection unit 130 includes a shift signal unit 131 and a difference signal output unit 133 in order to output a difference signal S(n)−S(n−1) of the original signal S(n) of the effective frame.

The shift signal unit 131 generates a shift signal S(n−1) by shifting the original signal S(n) of the effective frame, and the difference signal output unit 133 outputs a difference signal S(n)−S(n−1) between the original signal and the shift signal S(n−1).

As features before and after drinking, it has been reported that high-frequency components increase like characteristics of a nasal sound. That is, there is a significant difference in high-frequency components while low-frequency components almost do not change. Drinking causes auditory degradation. Accordingly, a speaker should speak with a loud voice and thus open his or her mouth wide because the speaker would not be able to hear well. This increases the lung capacity and affects energy. In addition, when the speaker is drunk, the volume of their voice cannot be maintained and usually increases or decreases excessively. Accordingly, a deviation in the volume of the voice increases after drinking.

According to the present invention, a difference signal of an original signal is found. The found difference signal shows a characteristic that high-frequency components are highlighted. Therefore, the difference between before and after drinking may be further highlighted, and also a high-frequency analysis may be further facilitated by using the difference signal.

The energy detection unit 150 detects average energy of the original signal S(n) for each effective frame and also detects average energy of the difference signal S(n)−S(n−1) for each effective frame.

Figure 6:
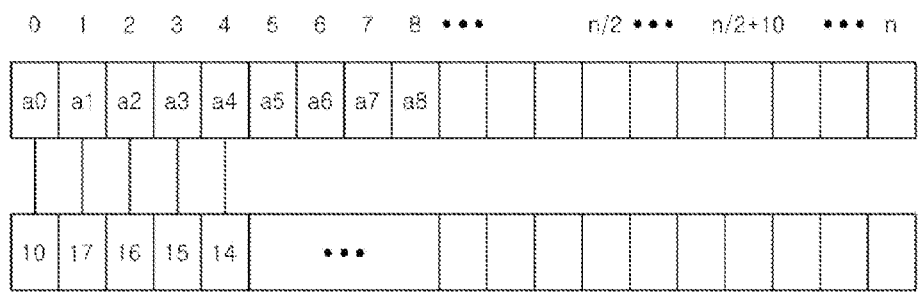
FIG. 6 is a view for describing an operation of an energy detection unit of FIG. 1.

Referring to FIG. 6, the average energy calculated by the energy detection unit 150 is calculated by summing the squares of N samples having short time energy n−N+1 to energy n with respect to sample n using Equation 1 below:

$$E_n = \frac{1}{N} \cdot \sum_{m=n-N+1}^{n} s^2(m).$$ [Equation 1]

Average energy for each of the voice frames determined as voiced sounds may be calculated through Equation 1. However, it will be appreciated that the average energy may be calculated using other well-known techniques.

The energy detection unit 150 may include a first energy detection unit 151 configured to detect the average energy of the original signal S(n) for each effective frame and a second energy detection unit 152 configured to detect the average energy of the difference signal S(n)−S(n−1) for each effective frame.

In this embodiment, the energy of the original signal S(n) of the effective frame and the energy of the difference signal S(n)−S(n−1) of the effective frame may be detected by a separate energy detection unit. However, in another embodiment, the energy detection unit 150 may detect the energy of the original signal S(n) of the effective frame and the energy of the difference signal S(n)−S(n−1) of the effective frame at the same time, in any order, or in sequence.

Average energy E1(n) of an original signal S(n) of an nth effective frame and average energy E2(n) of a difference signal S(n)−S(n−1) of the nth effective frame are output to the alcohol consumption determination unit 170.

The alcohol consumption determination unit 170 finds a difference between the average energy E1 of the original signal S(n) of the effective frame and the average energy E2 of the difference signal S(n)−S(n−1) of the effective frame to determine whether alcohol has been consumed.

When a person is drunk, his or her ability to control the volume of voice is reduced, resulting in an increased energy change of a high-frequency component. Thus, the alcohol consumption determination unit 170 may determine whether alcohol has been consumed according to a difference of the energy change of the high-frequency component during a certain period.

Figure 7:
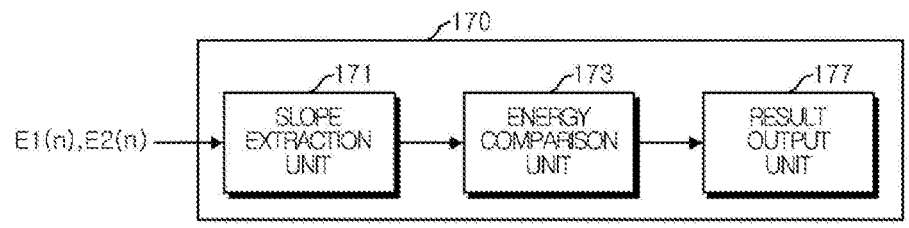
FIG. 7 is a detailed block diagram of an alcohol consumption determination unit of FIG. 1.

Referring to FIG. 7, the alcohol consumption determination unit 170 includes an energy comparison unit 171, a counting unit 173, and a result output unit 177.

For each effective frame, the energy comparison unit 171 compares the average energy of the original signal and the average energy of the difference signal and outputs a difference in the average energy. An average energy difference ER(n) of an nth effective frame may be calculated by Equation 2 below:

$ER(n) = \alpha \cdot (E1(n) - E2(n)) - \beta$ [Equation 2]

where E1(n) is average energy of an original signal S(n) of the nth effective frame, E2(n) is average energy of a difference signal S(n)−S(n−1) of the nth effective frame, and α and β are constants that are predetermined to more easily recognize the average energy difference.

The counting unit 173 counts the number of effective frames each having a difference ER(n) between the average energy of the original signal and the average energy of the difference signal greater than a predetermined first threshold. The first threshold may be predetermined and stored and also may be applied in all cases. The first threshold may be an optimal value that is set experimentally. Different first thresholds may be applied depending on gender or age or according to customization.

When the counted number of effective frames is greater than a predetermined second threshold, the result output unit 177 determines that alcohol has been consumed and outputs a result of the determination. For example, on a condition that the second threshold is set to five, the result output unit 177 determines that alcohol has been consumed when the number of effective frames each having a difference between the average energy of the original signal and the average energy of the difference signal greater than the predetermined first threshold is greater than five.

Although not shown in this embodiment, the alcohol consumption determination unit 170 may further include a storage unit configured to store the first threshold and the second threshold.

Figure 8:
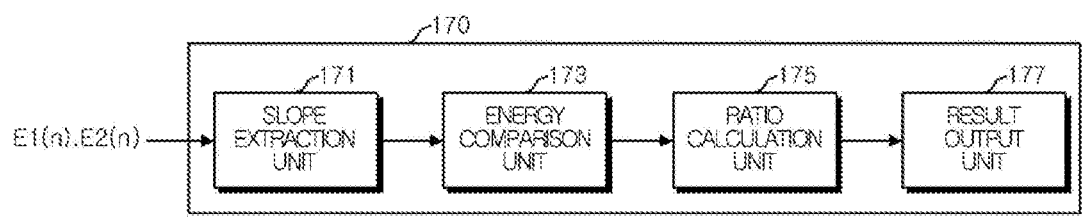
FIG. 8 is a detailed block diagram showing an alcohol consumption determination unit of a device for performing alcohol determination according to another embodiment of the present invention.

FIG. 8 is a detailed block diagram showing an alcohol consumption determination unit of a device for performing alcohol determination according to another embodiment of the present invention.

The alcohol consumption determination unit according to this embodiment may be substantially the same as the alcohol consumption determination unit of FIG. 7, except that the ratio calculation unit 175 is further included. Therefore, the same elements as those of the alcohol consumption determination unit of FIG. 7 are designated by the same reference numerals, and repetitive descriptions thereof will be omitted.

The ratio calculation unit 175 compares, with the total number of effective frames, the counted number of effective frames each having the difference ER(n) between the average energy of the original signal and the average energy of the difference signal greater than a predetermined first threshold to calculate a ratio between the two.

The ratio calculation unit 175 compares a result calculated by the counting unit 173 with the total number of effective frames (the total number of voice frames determined as voiced sounds) to calculate a ratio therebetween. The ratio calculation unit 175 may calculate a ratio R using Equation 3 below:

$$R = \frac{C}{T} \qquad \text{[Equation 3]}$$

where C is the counted number, and T is the total number of effective frames.

When the ratio R is greater than a predetermined third threshold, a change in energy of a high-frequency component is large. Accordingly, the result output unit 177 determines that alcohol has been consumed and outputs a result of the determination.

Figure 9:
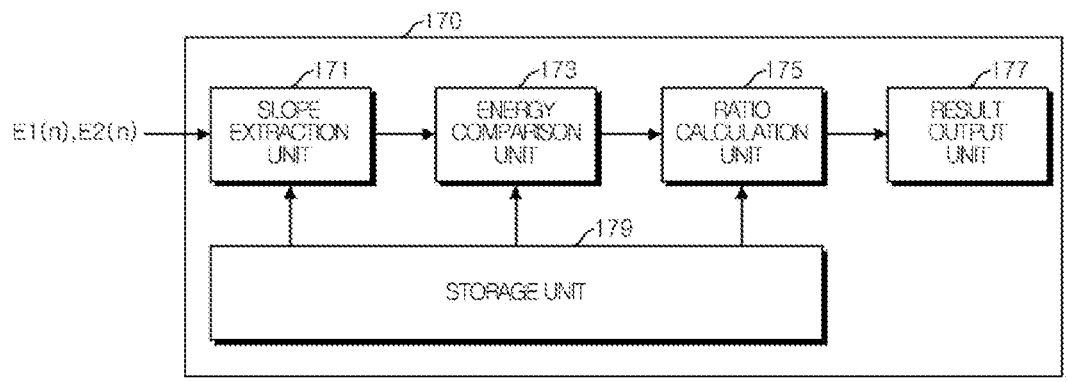
FIG. 9 is a detailed block diagram showing an alcohol consumption determination unit of a device for performing alcohol determination according to still another embodiment of the present invention.

FIG. 9 is a detailed block diagram showing an alcohol consumption determination unit of a device for performing alcohol determination according to still another embodiment of the present invention.

The alcohol consumption determination unit according to this embodiment may be substantially the same as the alcohol consumption determination unit of FIG. 8, except that the storage unit 179 is further included. Therefore, the same elements as those of the alcohol consumption determination unit of FIG. 8 are designated by the same reference numerals, and repetitive descriptions thereof will be omitted.

The storage unit 179 prestores at least one of the first threshold, the second threshold, and the third threshold. The first threshold, the second threshold, and the third threshold may be optimal values that are set experimentally. Different thresholds may be applied depending on gender or age or according to customization. In addition, the thresholds can be changed, deleted, stored, or added later.

The alcohol consumption determination device according to the present invention determines whether alcohol has been consumed within the duration of the voice signal. In particular, the alcohol consumption determination device utilizes a difference signal energy comparison method in order to highlight high frequencies of the voice signal and also increase analysis accuracy for the signal. This is intended to analyze a change in energy by minimizing low-frequency characteristics and highlighting high-frequency characteristics. An energy deviation is found for each frame by finding an average energy difference between the original signal and the difference signal. The average energy difference represents a characteristic of a drinker to be compared. Whether alcohol has been consumed is objectively determined using the average energy difference as a parameter.

Figure 10:
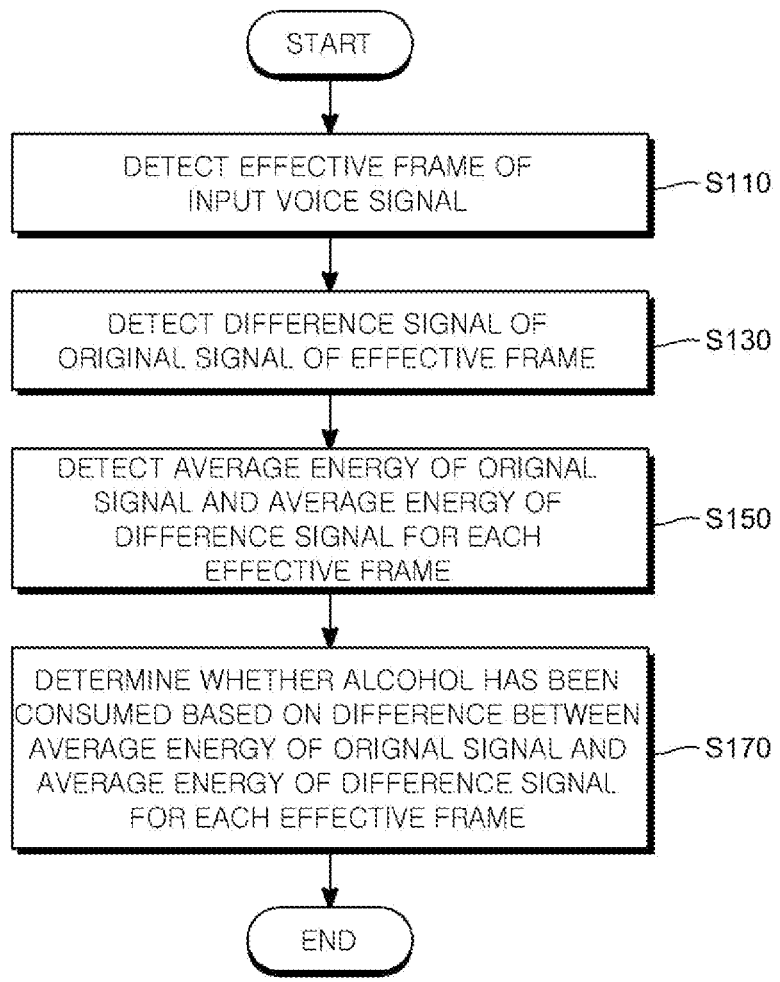
FIG. 10 is a flowchart showing an alcohol consumption determination method according to an embodiment of the present invention.

FIG. 10 is a flowchart showing an alcohol consumption determination method according to an embodiment of the present invention.

The alcohol consumption determination method according to this embodiment may be performed in substantially the same configuration as that of the device 10 of FIG. 1. Therefore, the same elements as those of the device 10 of FIG. 1 are designated by the same reference numerals, and repetitive descriptions thereof will be omitted.

Alternatively, the alcohol consumption determination method according to this embodiment may be executed by alcohol consumption determination software (application).

Referring to FIG. 10, the alcohol consumption determination method according to this embodiment includes detecting an effective frame of an input voice signal (step S110).

The step of detecting the effective frame (step S110) may include forming a voice frame of the input voice signal and determining whether the voice frame corresponds to a voiced sound.

In detail, the step may include receiving a person's voice, converting the voice into voice data, converting the voice data into voice frame data in units of a frame, and analyzing whether the voice frame is associated with a voiced sound, an unvoiced sound, or noise. According to a result of the analysis, only a frame corresponding to a voiced sound, that is, an effective frame may be output.

The method includes detecting a difference signal of an original signal of the effective frame when the effective frame is detected (step S130).

The step of detecting the difference signal (step S130) may include generating a shift signal S(n−1) by shifting the original signal S(n) of the effective frame and outputting a difference signal S(n)−S(n−1) between the original signal and the shift signal.

Since the difference signal shows a characteristic that high-frequency components are highlighted, the difference between before and after drinking may be further highlighted, and also the analysis of high frequencies may be further facilitated by using the difference signal.

The method includes detecting average energy of the original signal and average energy of the difference signal for each effective frame (step S150).

The step of detecting the average energy (step S150) may include detecting the average energy of the original signal for each effective frame and detecting the average energy of the difference signal for each effective frame.

Unlike this, average energy E1(n) of an original signal of an nth effective frame and average energy E2(n) of a difference signal of the nth effective frame may be detected at the same time, in any order, or in sequence.

The method includes determining whether alcohol has been consumed based on a difference between the average energy E1(n) of the original signal of the nth effective frame and the average energy E2(n) of the difference signal of the nth effective frame (step S170).

The step of determining whether alcohol has been consumed (step S170) may include comparing average energy of the original signal and average energy of the difference signal for each effective frame and outputting a difference in the average energy, counting the number of effective frames each having the difference between the average energy of the original signal and the average energy of the difference signal greater than a predetermined first threshold; and determining that alcohol has been consumed when the counted number of effective frames is greater than a predetermined second threshold and outputting a result of the determination.

In another embodiment, the step of determining whether alcohol has been consumed (step S170) may include comparing average energy of the original signal and average energy of the difference signal for each effective frame and outputting a difference in the average energy, counting the number of effective frames each having the difference between the average energy of the original signal and the average energy of the difference signal greater than a predetermined first threshold; comparing the counted number of effective frames with the total number of effective frames to calculate a ratio therebetween; and determining that alcohol has been consumed when the ratio is greater than a predetermined third threshold and outputting a result of the determination.

In addition, at least one of the first threshold, the second threshold, and the third threshold may be predetermined and stored, and also may be applied in all cases. The thresholds may be optimal values that are set experimentally. Different thresholds may be applied depending on a gender or an age or according to customization.

As described above, the alcohol consumption determination method may be implemented as an application or implemented in the form of program instructions that may be executed through various computer components and recorded on a computer-readable recording medium. The computer-readable recording medium may include program instructions, data files, data structures, and the like individually or in combination.

The program instructions recorded on the computer-readable recording medium may be specifically designed for the present invention or may be well-known to and used by those skilled in the art of computer software.

Examples of the computer-readable recording medium include a magnetic medium such as a hard disk, a floppy disk, or a magnetic tape, an optical medium such as a compact disc-read only memory (CD-ROM) or a digital versatile disc (DVD), a magneto-optical medium such as a floptical disk, and a hardware device such as a ROM, a random access memory (RAM), or a flash memory that is specially designed to store and execute program instructions.

Examples of the program instructions include not only machine code generated by a compiler or the like but also high-level language codes that may be executed by a computer using an interpreter or the like. The hardware device may be configured to operate as one or more software modules in order to perform operations of the present invention, and vice versa.

Although the present invention has been described with reference to exemplary embodiments, it will be understood that various changes and modifications may be made herein without departing from the scope and spirit of the present invention defined in the appended claims.

INDUSTRIAL APPLICABILITY

The alcohol consumption determination method according to the present invention, recording medium, and device for implementing the same may determine whether, from a remote location, a driver or operator has consumed alcohol through communication, thus preventing an accident caused by a operation vehicles and machines while under the influence of alcohol. In addition, the present invention may be widely applied to transportation areas such as vessels, rail roads, aircrafts, vehicles, buses, and highways, scernarios that make it difficult to determine to degree of inebriation, also for domestic and foreign vessel and air control service systems. Furthermore, the present invention may contribute to a web application on a personal cellular phone for measuring alcohol consumption.

The invention claimed is:

1. A computer implemented method for determining whether alcohol is consumed by a person by using at least one processor for executing a specific computer software to perform steps comprising:
   receiving an input voice signal from said person via a microphone sensor;
   forming a voice frame of the input voice signal;
   determining whether the formed voice frame corresponds to a voiced sound;
   forming a plurality of effective frames by converting the input voice signal from said person according to a result of the voiced sound determination;
   generating an original signal of each of the plurality of effective frames and a difference signal of the original signal;
   computing a first average energy of the original signal and a second average energy of the difference signal for each of the plurality of effective frames; determining whether alcohol is consumed by said person based on a difference between the first average energy and the second average energy, and
   outputting a result of a determination whether alcohol is consumed by said person who is located in a remote location.

2. The computer implemented method of claim 1, wherein the determining whether the formed voice frame corresponds to the voiced sound comprises:
   extracting periodic characteristics of harmonics or features from the formed voice frame, and
   determining whether the formed voice frame is from the voiced sound, an unvoiced sound, or background noise based on the extracted periodic characteristics of harmonics or features.

3. The computer implemented method of claim 2, wherein periodic characteristics of harmonics or features comprise root mean square energy (RMSE) or zero-crossing count (ZC) of a low-band voice signal energy area.

4. The computer implemented method of claim 3, wherein the determining whether the formed voice frame is from the voiced sound, an unvoiced sound, or background noise based on the extracted periodic characteristics of harmonics or features comprises use of neural network.

5. The computer implemented method of claim 1, wherein the generating an original signal of each of the plurality of effective frames and a difference signal of the original signal comprises:
   generating an original signal S(n) of the formed effective frame;
   generating a shift signal S(n−1) by shifting the original signal S(n); and
   generating a difference signal S(n)−S(n−1) between the original signal S(n) and the shift signal S(n−1).

6. The computer implemented method of claim 5, wherein the difference signal S(n)−S(n−1) comprises a characteristic of highlighting high-frequency components.

7. The computer implemented method of claim 1, wherein the computing the first average energy of the original signal and the second average energy of the difference signal for each of the plurality of effective frames comprises:
computing the first average energy of the original signal for each of the plurality of effective frames; and
computing the second average energy of the difference signal for each of the plurality of effective frames.

8. The computer implemented method of claim 1, wherein the determining whether alcohol is consumed by said person based on the difference between the first average energy and the second average energy comprises:
calculating a difference between the first average energy and the second average energy for each of the plurality of effective frames;
counting the number of effective frames each having the calculated difference greater than a predetermined first threshold; and
determining that alcohol is consumed by said person when the counted number is greater than a predetermined second threshold and outputting a result of the determination.

9. The computer implemented method of claim 1, wherein the determining whether alcohol is consumed by said person based on the difference between the first average energy and the second average energy comprises:
calculating the difference between the first average energy and the second average energy for each of the plurality of effective frames;
counting the number of effective frames each having the calculated difference greater than a predetermined first threshold;
computing a ratio between the counted number and the total number of effective frames; and
determining that alcohol is consumed by said person when the computed ratio is greater than a predetermined third threshold and outputting a result of the determination.

10. A non-transitory computer-readable recording medium having a computer program recorded thereon for performing the method of claim 1 of determining whether alcohol is consumed by said person.

11. A computer implemented device including at least one processor for executing a specific computer software to determine whether alcohol is consumed by a person, the computer implemented device comprising:
a microphone sensor receiving an input voice signal from said person;
a frame forming unit configured to form a voice frame of the input voice signal from said person;
a voiced sound determination unit configured to determine whether the voice frame corresponds to a voiced sound;
an effective frame detection unit configured to detect a plurality of effective frames by converting the input voice signal from said person according to a result of the voiced sound determination;
a difference signal detection unit configured to detect a difference signal of an original signal of each of the plurality of effective frames;
an energy detection unit configured to detect a first average energy of the original signal and a second average energy of the difference signal for each of the plurality of effective frames; and
an alcohol consumption determination unit configured to determine whether alcohol is consumed by said person based on a difference between the first average energy of the original signal and the second average energy and output a result of a determination whether alcohol is consumed by said person who is located in a remote location.

12. The computer implemented device of claim 11, wherein the difference signal detection unit comprises a shift signal unit configured to generate a shift signal S(n−1) by shifting the original signal S(n) of the effective frame; and a difference signal output unit configured to output a difference signal S(n)−S(n−1) between the original signal and the shift signal.

13. The computer implemented device of claim 11, wherein the energy detection unit comprises:
a first energy detection unit configured to compute the first average energy of the original signal for each of the plurality of effective frame; and
a second energy detection unit configured to compute the second average energy of the difference signal for each of the plurality of effective frame.

14. The computer implemented device of claim 11, wherein the alcohol consumption determination unit comprises:
an energy comparison unit configured to calculate the difference between the first average energy and the second average energy for each of the plurality of effective frames and outputting the calculated difference;
a counting unit configured to count the number of effective frames each having the calculated difference greater than a predetermined first threshold; and
a result output unit configured to determine that alcohol is consumed by said person when the counted number is greater than a predetermined second threshold and outputting a result of the determination.

15. The computer implemented device of claim 14, wherein the alcohol consumption determination unit further comprises a storage unit configured to prestore at least one of the first threshold and the second threshold.

16. The computer implemented device of claim 11, wherein the alcohol consumption determination unit comprises:
an energy comparison unit configured to calculate the difference between the first average energy and the second average energy for each of the plurality of effective frames and outputting the calculated difference;
a counting unit configured to count the number of effective frames each having the calculated difference greater than a predetermined first threshold;
a ratio calculation unit configured to compute a ratio between the counted number and the total number of effective frames; and
a result output unit configured to determine that alcohol is consumed by said person when the computed ratio is greater than a predetermined third threshold and outputting a result of the determination.

17. The computer implemented device of claim 16, wherein the alcohol consumption determination unit further comprises a storage unit configured to prestore at least one of the first threshold and the third threshold.

18. A portable computer implemented device comprising the computer implemented device of claim 11 for determining whether alcohol is consumed by said person.

* * * * *